United States Patent [19]
Sanders et al.

[11] Patent Number: 5,889,397
[45] Date of Patent: Mar. 30, 1999

[54] AUTOMATIC HTS FORCE MEASUREMENT INSTRUMENT

[75] Inventors: Scott T. Sanders, Valparaiso, Ind.; Ralph C. Niemann, Downers Grove, Ill.

[73] Assignee: The University of Chicago, Chicago, Ill.

[21] Appl. No.: 833,923

[22] Filed: Apr. 10, 1997

[51] Int. Cl.⁶ ................................. G01N 27/00
[52] U.S. Cl. ........................... 324/71.6; 73/819
[58] Field of Search ............... 324/71.6; 73/819, 73/824

[56] References Cited

U.S. PATENT DOCUMENTS 3,368,674  2/1968  Koeppe ............................ 73/819
3,885,421  5/1975  Nakamura ......................... 73/824

*Primary Examiner*—Josie Ballato
*Assistant Examiner*—Jose M. Solis
*Attorney, Agent, or Firm*—Emrich & Dithmar

[57] ABSTRACT

A device for measuring the levitation force of a high temperature superconductor sample with respect to a reference magnet includes a receptacle for holding several high temperature superconductor samples each cooled to superconducting temperature. A rotatable carousel successively locates a selected one of the high temperature superconductor samples in registry with the reference magnet. Mechanism varies the distance between one of the high temperature superconductor samples and the reference magnet, and a sensor measures levitation force of the sample as a function of the distance between the reference magnet and the sample. A method is also disclosed.

16 Claims, 3 Drawing Sheets

5,889,397

AUTOMATIC HTS FORCE MEASUREMENT INSTRUMENT

The United States Government has rights in this invention pursuant to Contract No. W-31-109-ENG-38 between the U.S. Department of Energy and The University of Chicago representing Argonne National Laboratory.

SUMMARY OF THE INVENTION

This invention relates to a machine which measures the quality of HTS (high-temperature superconductor) samples used for levitation purposes.

BACKGROUND OF THE INVENTION

To quantify the levitation force of HTS samples in the presence of an external magnetic field, a measurement process has evolved. This process, shown in FIG. 1 labeled Previous Testing Method, involves zero-field-cooling a sample 10 in a dish containing a liquid cryogen, such as nitrogen, then moving a reference magnet 12 towards the sample 10 and measuring the repulsive force exerted on the magnet at precise distances from the sample. The force is measured using a load cell 13; the distance is measured and changed using a motion controller system and stage 15. In general, a force vs. separation distance hysteresis curve is generated by use of a well known program entitled "Labview" put out by National Instruments of Austin, Tex., and the curve is extrapolated to a distance of zero. The force at zero distance is termed $F_o$, and this number is representative of the levitation quality of a given HTS sample.

This measurement heretofore has been performed on one sample at a time. Prior to the subject invention each sample was cemented upright in a Styrofoam dish and cooled with liquid nitrogen. The load cell/magnet probe approached the sample from above to acquire the necessary data. Lengthy set-up times, manual control of liquid nitrogen addition, and cool-down time for each HTS sample ready to be tested made the process slow to produce results, repetitive to perform, and ultimately inaccurate due to human error.

When more samples began accumulating for use such as in an FES (flywheel energy storage) facility, an improved testing method was needed. Preferably, the new method would use the same measurement principles and generate the same curves, but do so more efficiently and accurately.

The machine of the present invention was designed to be loaded with a plurality of samples, each sample preferably being a hexagonally shaped disc, and to provide one hysteresis curve and $F_o$ value for each sample, as quickly and accurately as possible. Because of cost and accuracy considerations, only one load cell/magnet probe was used although more are possible, and the samples were to be tested seriatim.

Accordingly, it is an object of the present invention to provide a machine for determining hysteresis curves and $F_o$ values for HTS samples more rapidly than heretofore possible.

Another object of the invention is to provide a machine for determining hysteresis curves and $F_o$ values for HTS samples in which a plurality of samples are tested seriatim without the need for individual supervision.

Still another object of the present invention was to provide a machine for determining hysteresis curves and $F_o$ values for a plurality of HTS samples which can easily be adapted to continuous through semi-continuous modes of operation.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DESCRIPTION OF THE PREFERRED EMBODIMENT

Figure 1:
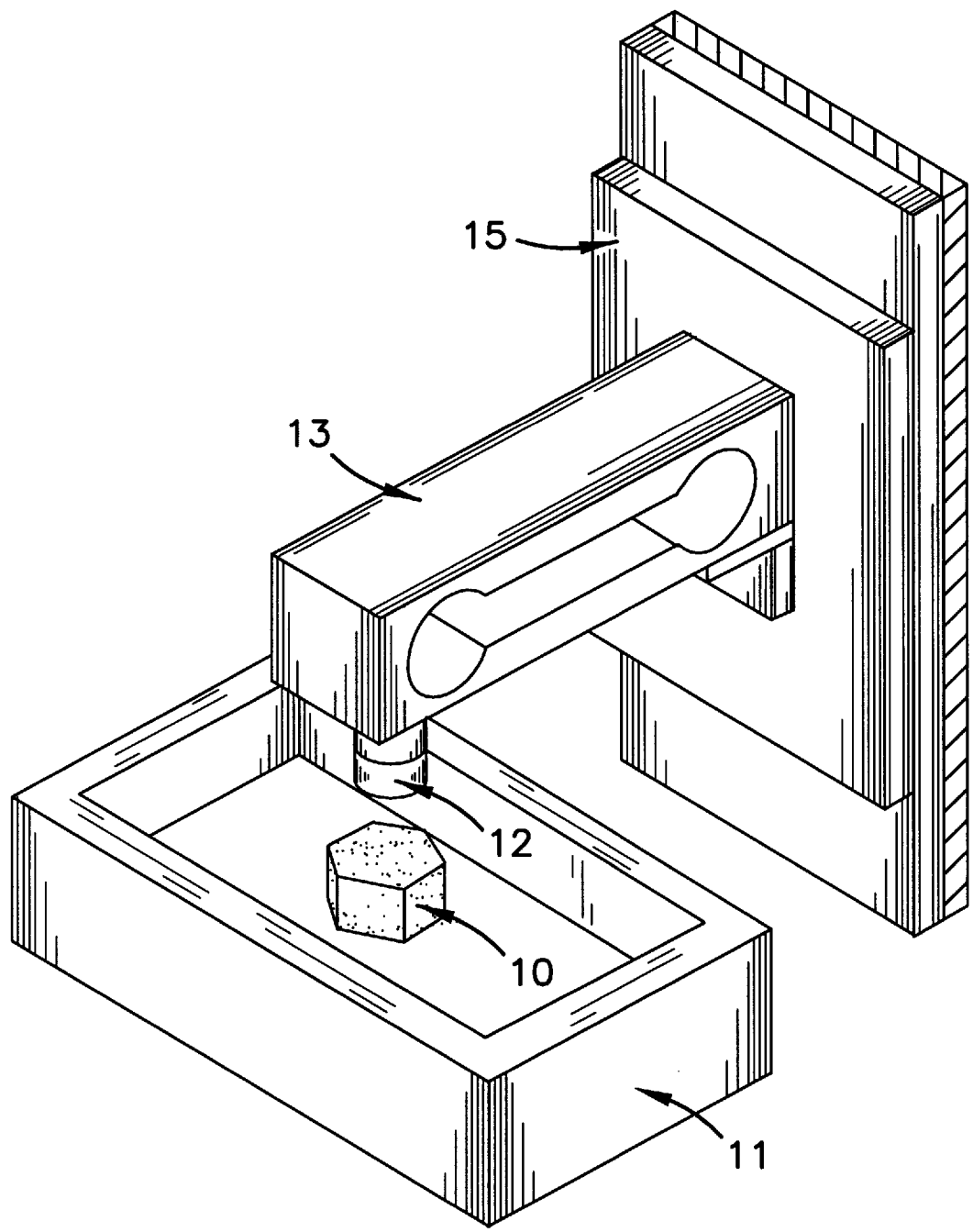
FIG. 1 is a isometric view of a prior art mechanism for testing HTS samples.
Figure 2:
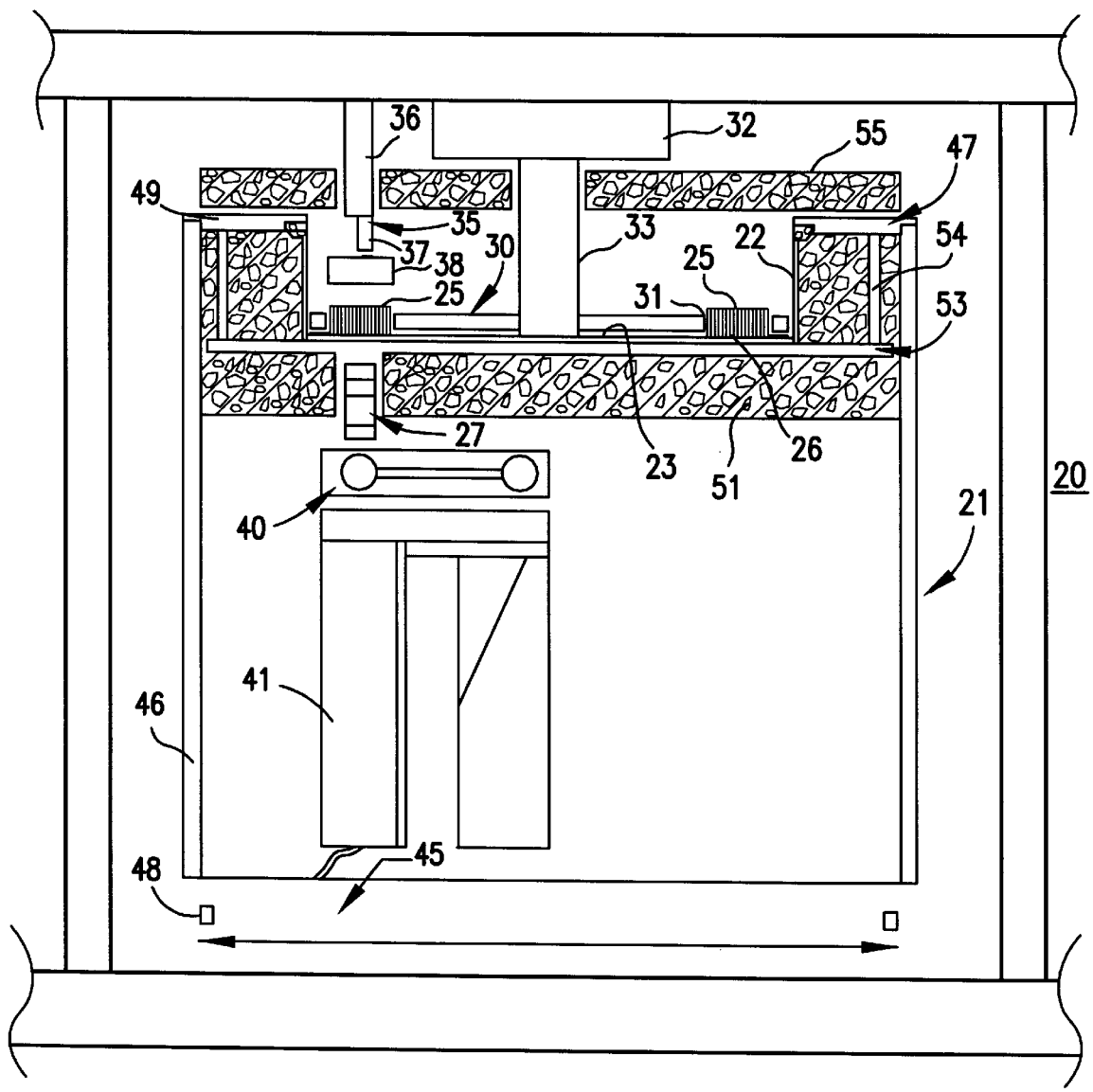
FIG. 2 is a cross section of the inventive device.

A cross-section of the invention is shown in FIG. 2. The machine 20 includes a sealed cryochamber 21 having a leak-tight pan 22 having an inner bottom surface 23 to hold a cryogen such as liquid nitrogen and a plurality of such as ten HTS samples 25. Because the samples 25 have a top side 26 which outperforms their bottom sides in these measurements, it is important that the samples 25 are placed into the pan 22 with their top sides 26 down. Contrary to the prior art, the hexagonal top side 26 of the sample 25 shown in FIG. 2 must face a magnet 27, which in the machine 20 requires placing the sample 25 upside-down in the pan 22. The samples 25 are indexed by a rotary table or carousel 30 having a plurality of circumferentially spaced apertures 31 coupled to a motion controller stage 32 by a shaft 33. The motion controller system and stage 32 was purchased from Newport and identified as Model No. M-495. The samples 25 are slid along the bottom surface 23 of the pan 22, which is always stationary.

Figure 3:
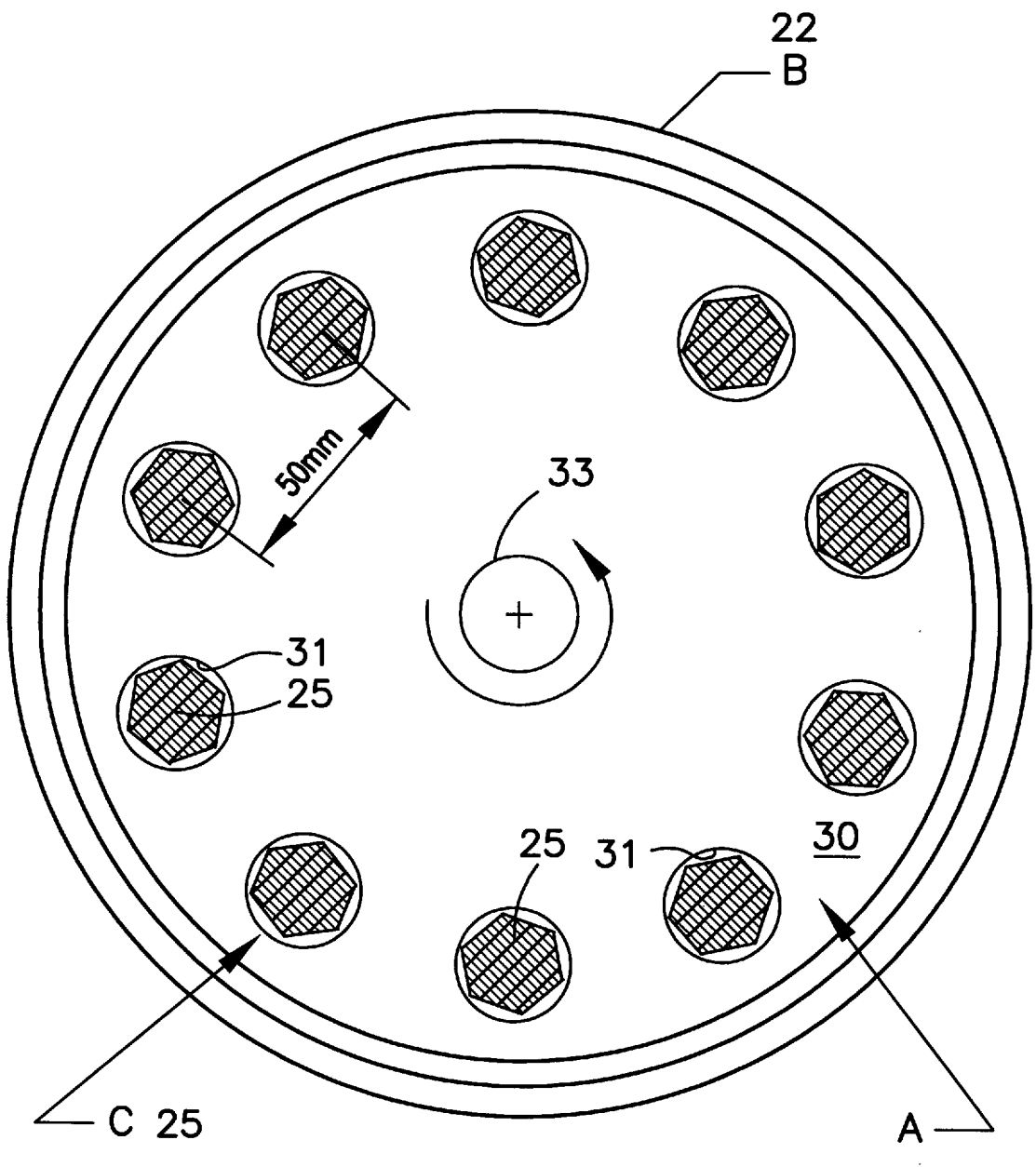
FIG. 3 is a plan view of a carousel useful in the present invention with multiple HTS samples.

A top view of the rotary table or carousel 30, pan 22, and samples 25 is shown in FIG. 3. As shown in FIG. 2, the sample 25 ready for testing is positioned below a mechanically actuated mechanism, such as an air-cylinder mechanism 35 having an air cylinder 36, a shaft 37 and a disc 38. The shaft 37 of plunger mechanism 35 is extended after a sample 25 is positioned for testing in order to hold the sample 25 firmly against the bottom 23 of the pan 22, to counteract the repulsive force exerted by the magnet 27 during testing. The magnet 27 is attached to a load cell 40 and the entire load cell/magnet probe is indexed vertically by a linear screw actuator 41. The load cell 40 was obtained from BLH Electronics, Model No. C2616K and the linear screw actuator was obtained from Newport, Model No. M-360-90.

In order to test a HTS sample 25, the sample is rotated into position by the table or carousel 30 by operation of the motion controller 32, then locked down by the plunger mechanism 35. The load cell 40 and magnet probe 27 (which is at a known distance from the sample, often 15 mm) begins approaching the sample 25, and force vs. separation data is collected at precise intervals. The magnet 27 approaches to a minimum separation distance, often 1 mm since the particular pan 22 used had a wall thickness of 0.737 mm. Then the magnet 27 is returned to its original position, collecting data again at precise intervals. Several variations of this test, all providing force hysteresis data, can be accommodated by the mechanism 20. The plunger mechanism 35 is lifted, the tested sample 25 is rotated away, and the next sample is indexed into position. This process is repeated a predetermined number of times before reloading is necessary.

Condensation on the cold bottom surface 23 of the pan 22 would interfere with the magnet 27 travel and force measurements. To alleviate this problem, the entire region below the pan 22 is purged with a high-purity nitrogen gas. As an alternative to purging, a vacuum could be drawn in this region, eliminating condensation and also improving thermal insulation. The sealed purge chamber 21 consists of a suitable plastic, such as polyvinyl chloride (PVC) bottom mounting plate 45, transparent plastic, such as acrylic, tube 46, enclosed at the top by a support ring 47 of a suitable material such as epoxy-fiberglass composite (i.e. NEMA-grade G-10), and the pan 22. The temporary seal at the bottom is accomplished with an O-ring 48. The seal between the tube 46 and support 47 is a permanent joint 49, of a suitable material such as an epoxy resin. The G-10 ring 47 is sealed to the pan 22 using the closed-cell Styrofoam 51 and vacuum grease. A clamp 53 locks the pan 22 to the ring 47 with bolts 54 passing through the Styrofoam 51. A Styrofoam lid 55 is also placed on the device 20 during testing; both Styrofoam pieces 51, 55 provide thermal insulation to conserve liquid nitrogen in the pan. While various specific plastics have been used herein, they are named for purposes of illustration only. Other plastics are available which would be acceptable alternatives.

The primary advantages of the subject invention over previous force-measuring techniques are improved speed, accuracy and efficiency while saving operating costs.

The magnet 27 is never in direct contact with liquid nitrogen, so its temperature is more consistent during testing than in previous measurement schemes. A magnet's field varies with temperature, so improved temperature stability ultimately translates into reliable and repeatable force measurements. In previous techniques, when HTS samples 25 were measured from above in an open dish, the magnet occasionally contacted free cryogen near the sample, and at this point its force measurements became unreliable.

The HTS samples 25 in the present invention are at the bottom rather than the top of the liquid nitrogen bath so their temperature is constant and results are more repeatable. When measuring the sample from above, as was the protocol in previous measurements, the top surface of the sample was left exposed so the magnet could approach, and liquid nitrogen level varied because it was controlled by an operator. This resulted in inconsistent temperature of HTS samples which translated into less reliable and repeatable data.

The present method of determining the position of the load cell/magnet probe 40, 27 is improved over previous techniques. The measurement of the separation distance between the magnet 27 and the HTS sample 25 is critical to achieving correct $F_o$ values. A reliable measurement can be achieved by zeroing the magnet 27 against a reference surface and relying on accurate motion controller systems to report its position. In previous procedure, the magnet was zeroed against the surface of the warm HTS sample to be tested. Then, when liquid nitrogen was added so force measurements could be made, the dish holding the sample and liquid nitrogen contracted, moving the sample downward, and all position values thus became erroneous. Magnetic interaction between the probe and the sample prohibited zeroing the magnet against the sample after adding liquid nitrogen.

In the machine 20, the magnet 27 is "zeroed" against the bottom 23 of the pan 22 rather than the sample 25. This is done after the pan 22 has been filled with liquid nitrogen and has contracted, but before it contains any HTS samples 25. The magnet 27 can be "zeroed" against the bottom surface 23 of the pan 22 when the pan 22 is cold since there is no nearby HTS material for the magnet to interact with. The position of the magnet 27 is not actually set to zero when it contacts the pan 22, but is set to 0.737 mm, the thickness of the pan 22. Then, when a sample 25 is being tested, the distance between the magnet 27 and the top surface 26 of sample 25 is known, since the top surface 26 of sample 25 is pressed to the inner bottom surface 23 of the pan 22, and both the pan thickness and the distance between the magnet 27 and the top surface 26 of the sample 25 are known.

Because the measurement is made through the same section of the cryochamber pan 22 for each sample 25, determining the position of the magnet 27 with respect to the sample 25 is simple as well as accurate. The magnet zero is set once and is maintained through the heights of HTS samples 25 may vary drastically. This is because the samples 25, top (or measured) surfaces 26 are always in the same location pressed against the pan inner surface bottom 23, when the sample 25 is being tested. Also, the zero is set after the entire device 20 reaches a thermal steady state, so it never needs to be reset in response to thermal contraction, except after the pan 22 is rewarmed. There is no limit to the number of samples 25 that can be tested before rewarming the pan 22. With prior art methods, zeroing the magnet probe took approximately 2 minutes per HTS sample; whereas this delay is entirely eliminated by the subject invention.

The delay for cooling each sample 25 between individual sample tests is also eliminated. Ten samples 25 were loaded into the device 20 at once by an operator, and at the same time the operator replaced the small amount of cryogen that boiled off during the previous run with fresh liquid nitrogen. This ensured that the pan 22 always contained plenty of liquid nitrogen to zero-field cool the samples 25 at the time of loading and to keep them cold through the duration of the test. When one HTS sample 25 was finished testing, it is indexed out of position, and the next one is slid into the testing location. It was already cool and testing began immediately. The time spent cooling HTS samples 25 for testing was approximately 1 minute per sample in the previous testing procedure; now this 1 minute is spent cooling not one but all ten samples 25 during the loading period, reducing this delay drastically.

The efficiency of the loading operation has improved with the subject invention. Each sample 25 was placed into a circular slot 31 as the indexing table or carousel 30 was rotated 360 degrees. This entire loading took approximately 20 seconds. In previous methods, each sample 25 had to be cemented into place using vacuum grease because a hold-down system like the subject invention has was not easily adaptable to testing from above. It took approximately 1 minute per sample to prepare tests this way. Preparation in the device 20 required about 2 seconds per sample in a single loading operation, and the samples need not be cleaned of vacuum grease after testing.

In high-volume applications, the device 20 could be easily modified to automatically load HTS samples 25 continuously rather than interrupting testing for 2 minutes after every ten are tested. As each sample 25 is finished testing and indexed out of position, a mechanical hand (not shown) could be programmed to pull it out of the slot and replace it with a new HTS sample 25 awaiting testing on a conveyor belt (also not shown). In the current operating procedure, identification of the samples 25 after testing relies on preserving an order as they are placed into and removed from the device's pan 22. However, HTS samples 25 could be barcoded prior to testing and packaged in a manufacturing plant, and each sample's characteristics could be obtained easily when any consumer desired them.

While there has been disclosed what is considered to be the preferred embodiment of the present invention, it is understood that various changes in the details may be made without departing from the spirit, or sacrificing any of the advantages of the present invention.

The embodiments of the invention in which an exclusive property or privilege is claimed are defined as follows:

1. A device for measuring the levitation force of a high temperature superconductor sample with respect to a reference magnet maintained out of contact with a cryogenic-liquid, comprising a receptacle for holding a plurality of high temperature superconductor samples each cooled to superconducting temperature by contact with a cryogenic liquid, a positioning mechanism for successively locating a selected one of said high temperature superconductor samples in registry with said reference magnet, mechanism for varying the distance between said selected one of said high temperature superconductor samples and said reference magnet, and a sensor for measuring levitation force of said sample as a function of the distance between said reference magnet and said selected one of said high temperature superconducting samples.

2. The device of claim 1, wherein said sensor is operatively connected to said magnet.

3. The device of claim 1, wherein said receptacle has a predetermined wall thickness through which the levitation force is measured.

4. The device of claim 1, wherein said receptacle and said sample and at least a portion of said positioning mechanism are within an insulated compartment to enable said receptacle and said samples and said portion of said positioning mechanism to be maintained at superconducting temperatures during the measurement of levitation forces for all samples.

5. The device of claim 1, wherein said reference magnet is positioned below said receptacle and the high temperature superconductor sample to be measured is positioned in said receptacle and maintained in contact with the bottom of said receptacle during measurements of the levitation device.

6. The device of claim 1, wherein said positioning mechanism includes an apertured carousel connected to a motor mechanism for rotating the carousel to place a selected high temperature superconductor sample in registry with said reference magnet.

7. The device of claim 6, and further comprising thermal insulation surrounding said receptacle and said carousel for maintaining a plurality of high temperature superconductor samples and said receptacle and said carousel at the superconducting temperature during measurement of one sample.

8. A device for measuring the levitation force of a high temperature superconductor sample with respect to a reference magnet, comprising a receptacle for holding a plurality of high temperature superconductor samples each cooled to superconducting temperatures by contact with a cryogenic liquid, a positioning mechanism for successively locating a selected one of said high temperature superconductor samples in registry with said reference magnet, said reference magnet being physically separated from the cryogenic liquid, a thermally insulated chamber housing said receptacle and said samples and at least a portion of said positioning mechanism during measurement of levitation forces at superconducting temperatures, mechanism for varying the distance between said selected one of said high temperature superconductor sample and said reference magnet, a sensor for measuring the levitation force of said selected sample as a function of the distance between said reference magnet and said selected sample, and mechanism for recording the measured levitation force at a plurality of different distances between said reference magnet and selected sample to calculate the levitation force at zero distance.

9. The device of claim 8, wherein each high temperature superconductor sample is positioned on a bottom wall of said receptacle and held in place during measurement of the levitation force.

10. The device of claim 9, wherein a movable piston mechanism holds each sample against said receptacle bottom wall during measurement of the levitation force.

11. The device of claim 10, wherein said position mechanism includes a carousel having a plurality of circumferentially spaced openings each holding for holding a high temperature superconductor sample.

12. A method of measuring the levitation force of a plurality of high temperature superconductor samples, comprising providing a plurality of samples in a receptacle; cooling the samples to superconducting temperatures while maintaining the receptacle at substantially the same temperature as the samples; positioning one of the cooled samples in registry with a reference magnet, varying the distance between the reference magnet and the selected sample to obtain measurements of the levitation force of the selected sample, and thereafter positioning another one of the cooled samples in registry with the reference magnet.

13. The device of claim 9, wherein said reference magnet is moved toward and away from said bottom wall of said receptacle.

14. The device of claim 13, wherein a portion of thermal insulation around said receptacle is removed to permit said reference magnet to move toward and away from said bottom of said receptacle.

15. The method of claim 12, wherein the cooled sample being measured is maintained against the receptacle bottom wall during measurement of the levitation force.

16. The method of claim 15, wherein the reference magnet is moved toward and away from the receptacle bottom wall during measurement of the levitation force.

* * * * *